United States Patent [19]
Ferreira et al.

[11] Patent Number: 5,722,982
[45] Date of Patent: Mar. 3, 1998

[54] STRABISMUS SURGERY APPARATUS AND METHOD

[75] Inventors: Rosane Ferreira, Porto Alegre, Brazil; J. Bronwyn Bateman, Denver, Colo.; Tomas F. Scalamandré Mendonca, Sao Paulo, Brazil

[73] Assignee: University Technology Corporation, Boulder, Colo.

[21] Appl. No.: 721,279

[22] Filed: Sep. 26, 1996

[51] Int. Cl.[6] ........................................ A61B 17/00
[52] U.S. Cl. ...................... 606/151; 606/139; 606/142; 227/902
[58] Field of Search ...................... 606/151, 157, 606/158, 142, 139, 143, 150, 106, 116, 117, 161; 128/898, 831, 843; 227/902

[56] References Cited

U.S. PATENT DOCUMENTS

| | | |
|---|---|---|
| 2,437,812 | 3/1948 | Freel .................................. 606/151 |
| 4,414,985 | 11/1983 | Myer . |
| 4,469,101 | 9/1984 | Coleman et al. ...................... 606/151 |
| 4,519,392 | 5/1985 | Lingua .................................. 606/157 |
| 5,049,153 | 9/1991 | Nakao et al. ........................ 606/151 |
| 5,620,452 | 4/1997 | Yoon ...................................... 606/151 |

FOREIGN PATENT DOCUMENTS

| | | | |
|---|---|---|---|
| 0314412 | 5/1989 | European Pat. Off. ............... 606/151 |
| 80024 | 6/1919 | Switzerland ........................... 606/142 |

Primary Examiner—Jeffrey A. Schmidt
Attorney, Agent, or Firm—Rick Martin

[57] ABSTRACT

A new eye hook has a groove in the muscle engaging surface to house a muscle clip. Passage of the muscle clip under a muscle in a single step is made possible. The muscle clip has a smooth upper surface on the lower jaw to minimize friction with the muscle.

9 Claims, 5 Drawing Sheets

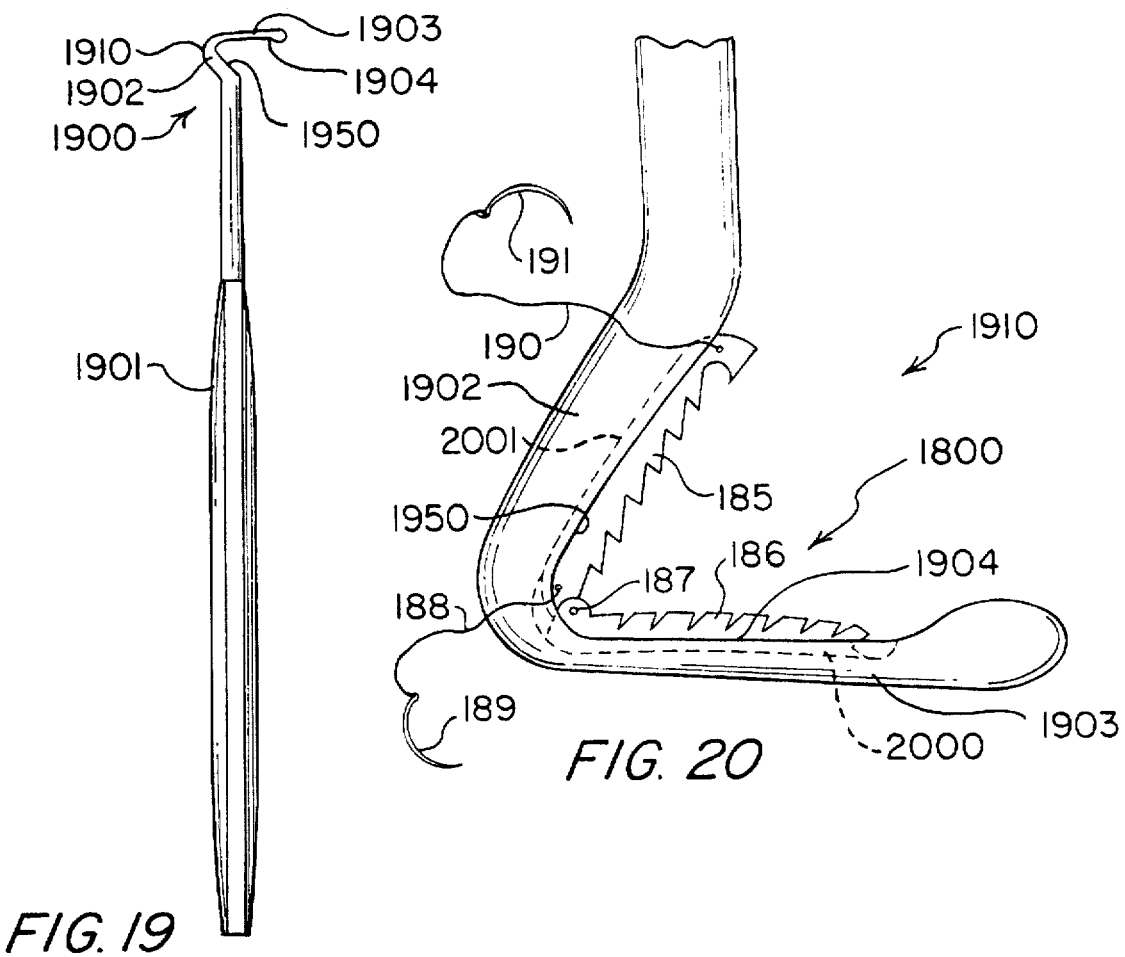
FIG. 19
FIG. 20
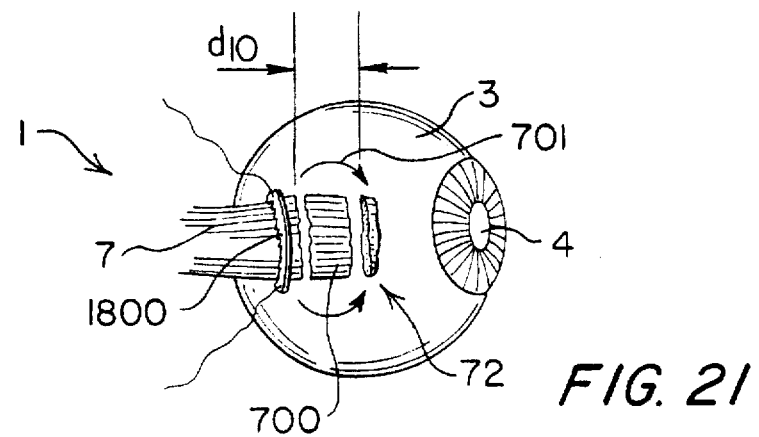
FIG. 21

STRABISMUS SURGERY APPARATUS AND METHOD

FIELD OF INVENTION

The present invention relates to a muscle combination muscle hook clip used in strabismus surgery to replace the traditional suture method.

BACKGROUND OF THE INVENTION

The term strabismus is used to describe eyes that are not straight or properly aligned. This misalignment results from the failure of the eye muscles to work together. One eye, or sometimes both, may turn in (crossed eyes), turn out (wall eyes), turn up, or turn down. Sometimes, more than one of the "turns" are present. The deviation may be constant or it may come and go. It may be present at birth, become apparent at a large age, or result after an illness or accident.

In order to understand strabismus, it is helpful to know how vision works. The process of vision is complex. The eye receives light waves which are focused on the retina (the rear lining of the eye) and transmitted from there to the brain. The brain, in turn, creates a single image from the separate ones it has received from the two eyes; this is known as fusion.

To develop normal, binocular (two-eyed) vision, a child needs two healthy, well-coordinated eyes with relatively equal vision in each so that the images that form on the retina will have comparable clarity. If the muscles that move each eyeball have developed correctly, the eyes will work together as a team.

If the eye muscles are not coordinated and one eye is looking directly at an object while the other turns in or out, the message from the eye that is on target will usually be stronger than the message from the other eye. As a consequence, the brain may simply ignore the weaker message. This solves the child's double vision problem, but creates another; the eye whose message is ignored develops weaker vision, amblyopia.

Strabismus may occur from several causes, such as birth injuries, heredity, faulty muscle attachments, need for glasses, excessive farsightedness, or body illnesses.

The major goals in treating strabismus are the development of normal vision in each eye, including fusion and depth perception. Accomplishing these goals often involve straightening the eyes and preventing amblyopia from developing.

Strabismus cannot be outgrown, nor will it improve by itself. Treatment to straighten the eyes is needed.

Surgery may be performed on the eye muscles to straighten the eyes if non-surgical means are unsuccessful.

There are three known surgical methods used to alter the force vectors applied to the globe of the eye by the surrounding muscle pairs.

Referring first to FIGS. 1, 3 the patient's nose is shown at 15, the left eye at 1, and the right eye at 8. The globes 3, 10 have pupils 4, 11 which are out of proper alignment as shown by arrows 2, 9. The medial rectus muscles 5, 12 are imparting different force vectors on the respective globes, thus causing the right eye 8 to turn in. The superior rectus muscles 6, 13, the lateral rectus muscles 7, 14, and the inferior rectus muscle 16 all appear to be normal.

Referring next to FIG. 2 the right eye 8 has been surgically repaired. All of the below discussed prior art surgical methods as well as the present invention seek to accomplish the identical surgical repair shown in FIG. 2. The medial rectus muscle 12 of FIG. 1 has been moved back on the globe 10 in direction 88. The globe 10 has turned in direction 89 by the relatively greater force applied by the lateral rectus muscle 14. The surgically repaired medial rectus muscle is shown as 120 in FIG. 2. Now the pupils 4, 11 are in proper alignment as shown by arrows 2, 90.

The traditional method of surgery (the suture method) begins in FIG. 4 as a traditional muscle hook 40 is placed under the left eye's medial rectus muscle 7. In FIGS. 5, 6, a needle 50 and suture material 51 are used to create a suture loop 510. This procedure is very difficult since the needle 50 can accidentally be poked into the globe 3. Also the suture loop 510 could be done incorrectly, thus pulling out of the muscle 7. In FIG. 7 a second needle 53 and suture material 54 has been fastened in a suture loop to the muscle 7. A surgeon holds the threads 51, 54 while a second surgeon uses the scissors 55 to cut the muscle 7. The tolerances are very tight as $d_1 = 1-2$ mm. Another risk is apparent here since the scissors could accidentally severe the suture loops and/or suture material. This could result in the muscle 7 retracting behind the globe 3, thus causing further surgical procedures to be applied to rescue the muscle 7.

In FIG. 8 the shortened medial rectus muscle is renumbered as 70. Medial rectus muscle 70 has a new insertion 71 as the needles and suture material 50, 51 and 53, 54 have sutured the muscle 70 to the sclera of the globe 3. The old insertion is shown as 72. This step completes the suture method of surgery.

The pros and cons of this method are summarized in the table below.

| Pros | Cons |
| --- | --- |
| 1. Proven method over 50 years old. | 1. Risk of cutting sutures and losing muscle. |
| 2. Inexpensive. | 2. Risk of perforating the globe. |
|  | 3. Time consuming to tie suture loops (about half an hour). |

Another known but rarely used method (not shown is to insert a clamp to grasp the muscle after the muscle hook 40 has been inserted. This is called the clamp method. No suture loops are made. The muscle is cut. Then the muscle is sutured directly to the sclera at the new insertion. The pros and cons of this method are summarized below.

| Pros | Cons |
| --- | --- |
| 1. Inexpensive. | 1. Time consuming. |
| 2. Using a reusable clamp reduces risk of perforating the globe. | 2. Risk of damaging muscle with the clamp. |
| 3. No risk of cutting sutures. | 3. Added skill needed to cut muscle flap to proper size because muscle flap tends to contract. |
|  | 4. Loss of shrunken muscle flap is forever. |
|  | 5. Risk of losing muscle out of the clamp. |

A patented method is taught in U.S. Pat. No. 4,519,392 (1985) to Lingua. No known use can be found. FIGS. 9–13 depict the Lingua method and apparatus. In FIG. 9, the muscle hook 40 is inserted as usual. In FIG. 10, the Lingua assembly 100 is attached to the muscle 7. The Lingua assembly consists of a first muscle clip 101 and a second muscle clip 102 which are connected together by suture materials 103, 104. The muscle clips 101, 102 are applied perpendicular to the muscle 7. The lengths of suture materials 103, 104 are predetermined at precisely the required length $d_2$ for the new insertion of the muscle 7 at 105 of FIG. 12. The scissors 55 cut the muscle between the muscle clips 101, 102. The final step is shown in FIG. 13 where tissue adhesive 130 is applied to the muscle 7 at insertion 105. The muscle 7 then grows to the sclera at insertion 105. No sutures are used.

The pros and cons of this method are summarized below.

| Pros | Cons |
| --- | --- |
| 1. No needle is used thus eliminating the risk of perforating the globe. | 1. Expensive (two clips) |
| 2. Ease of use to set the proper length of the suture thread members before surgery. | 2. Risk of tissue adhesive not taking. |
| 3. Reduces bleeding due to the hemostasing effect of the muscle clips. | 3. Tissue adhesive allows slippage of the muscle up and down before muscle adheres to the sclera. This causes up/down imbalance in the eyes. |
| | 4. Tissue adhesive allergies. |
| | 5. Tissue adhesive causes an unknown change in the length of the muscle flap which adheres to the sclera. This is called the arc of contact. Thus, only an imprecise muscle adjustment is possible. |
| | 6. Two clips mean two foreign bodies have to fit under the muscle. This may not be possible with tight muscles. |
| | 7. Risk of inflammatory reaction caused by two foreign bodies in the eye. |
| | 8. Risk of cutting suture material and losing the muscle. |

An alternate embodiment of the Lingua patent (taught at column 3, line 5 et seq. and column 6, line 53 et seq.) is similar to the suture method except that a single muscle clip is used instead of suture loops. Refer to FIGS. 14–17. First an eye hook 40 is passed under the muscle 7. Next a muscle clip is passed by hand under the muscle 7. Then the muscle 7 is cut and locked. Precise suturing of the muscle to the sclera is accomplished by supplying a needle and suture material to the muscle clip. The muscle is sutured to the sclera with the needles 151, 153 on the clip in a traditional manner using suture material 150, 152. The new insertion 71 is the same as shown in FIG. 8. The pros and cons of this one clip method are summarized below.

| Pros | Cons |
| --- | --- |
| 1. Faster since no suture loops are needed. | 1. Adds cost of muscle clips. |
| 2. Easier since suture loops require great skill. | 2. Risk of clip not holding muscle. |
| 3. Reduced risk of perforating the globe because suture loop step is eliminated. | 3. Adds a foreign body to the eye which can cause inflammatory reaction. |
| 4. Reduces muscle bleeding due to hemostasing effect of the muscle clip. | |

The present invention combines the one clip, Lingua method and apparatus with a modified muscle hook and an improved muscle clip. The modified muscle hook has a groove in the hook which houses the muscle clip, thereby enabling a single instrument to hook the muscle and pass the muscle clip underneath in one step. This embodiment is very useful when tight muscles are encountered. It also saves time and eliminates the step of separately passing a muscle hook under the eye.

A further improvement to the Lingua clip is also taught herein where the lower jaw of the clip is smooth to facilitate passing under the muscle.

SUMMARY OF THE INVENTION

The main object of the present invention is to provide a combination muscle hook and muscle clip holder tool which can perform traditional hook procedures as well as pass a Lingua clip under the muscle.

Another object of the present invention is to improve the Lingua clip by providing a smooth lower jaw and a pair of suture threads and needles on the clip.

Another object of the present invention is to provide a new surgical method using the new combination tool.

Other objects of this invention will appear from the following description and appended claims, reference being made to the accompanying drawings forming a part of this specification wherein like reference characters designate corresponding parts in the several views.

In the present invention, an improved Lingua clip has a smooth upper surface on the lower jaw. This smooth upper surface reduces friction when it is passed under the muscle. The new clip also has a pair of needles and suture material assemblies fastened one member on each end of the clip.

The clip is placed on a new combination hook and clip support. The combination hook and clip support has a groove on its lower leg and on its upper leg. The grooves house the clip for passage under the muscle in a single step. Thus, it is no longer necessary to first insert an eye hook and then pass a Lingua clip under the muscle. The preferred embodiment herein teaches a Lingua clip housed in a combination hook and clip support. the combination hook and clip support is passed under the muscle in a single step. For tight muscles, this assures that the Lingua clip can be passed underneath.

BRIEF DESCRIPTION OF THE DRAWINGS

FIG. 19 is a side plan view of the new combination hook and clip support tool.

FIG. 20 is a side plan view of the jaws of the combination hook and clip support tool housing a Lingua clip.

FIG. 21 is a side perspective view of the left eye showing a muscle segment removal procedure.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Figure 18:
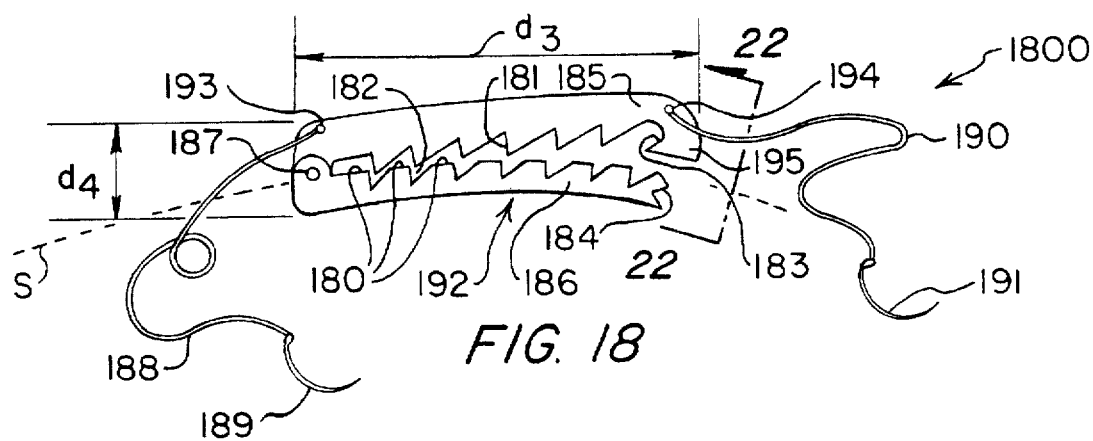
FIG. 18 is a side plan view of the improved Lingua clip.

Referring first to FIG. 18 a muscle clip (called a Lingua clip) 1800 has an upper jaw 185, a lower jaw 186, upper teeth 181 and lower recesses 182 for receiving upper teeth 181. A hinge 187 joins the upper and lower jaws. The lower jaw has an upper surface 180 which is smooth as indicated by dotted line S. The lower surface 192 of lower jaw 186 has an arcuate shape to substantially conform to the curvature of an eye. Holes 193, 194 support suture material 188, 190 which support needles 189, 191 respectively. Clip length d3 varies from about 6 to 8 mm according to the size of the muscle having surgery. The height d4 also varies from about 1 to 1.5 mm. To lock the Lingua clip 1800 closed, the upper jaw has a hook 195 and having a locking surface 183. The locking surface 183 snaps over ledge 184 of the lower jaw. Other known locking mechanisms would include a strap having arrow-like protuberances sliding into a clip.

Figure 1:
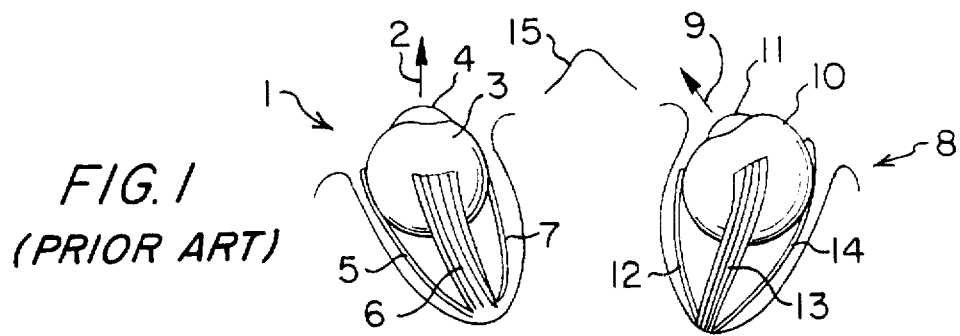
FIG. 1 (prior art) is a top-perspective view of a pair of crossed eyes.
Figure 2:
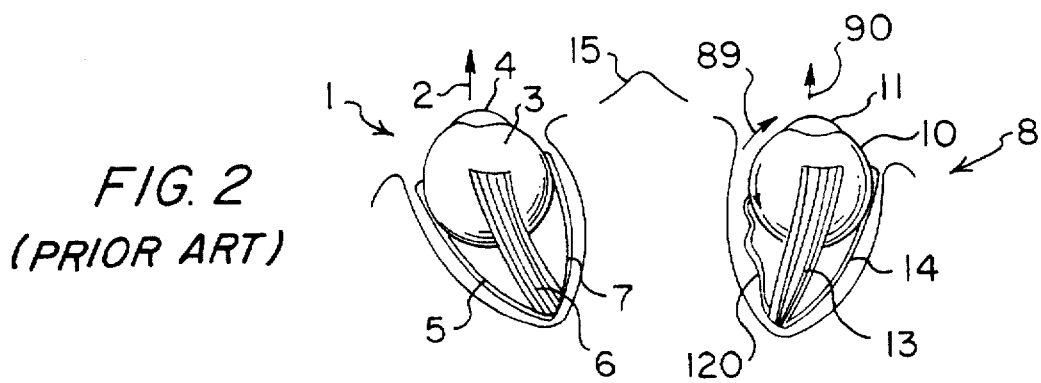
FIG. 2 (prior art) is a top perspective view of the pair of eyes of FIG. 1 after corrective strabismus surgery.
Figure 3:
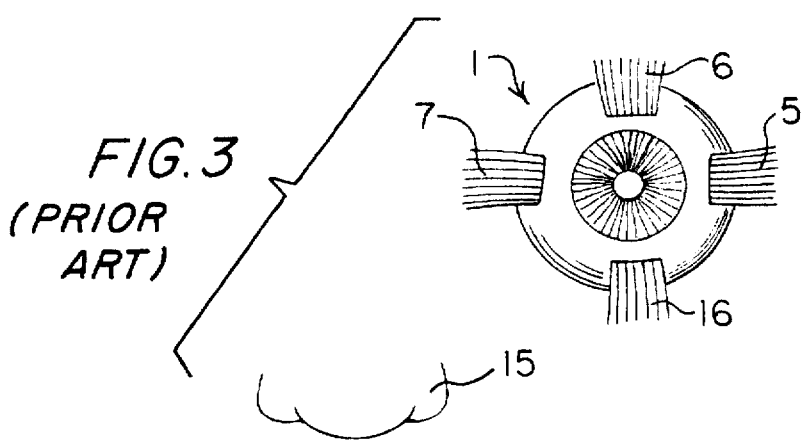
FIG. 3. (prior art) is a front plan view of a left eye.
Figure 4:
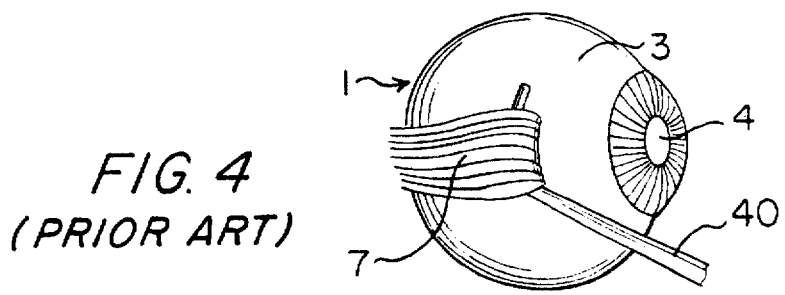
FIG. 4. (prior art) is a right side perspective view of the left eye having an eye hook under the medial rectus muscle.
Figure 5:
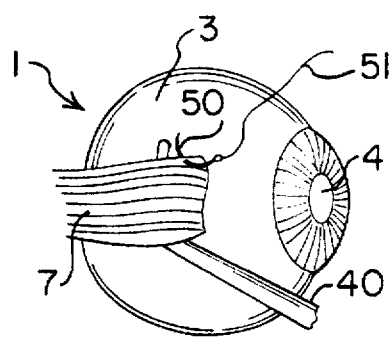
FIG. 5 (prior art) is the same view as FIG. 4 showing a needle and suture material in the medial rectus muscle.
Figure 6:
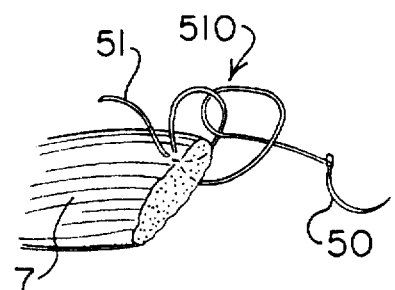
FIG. 6 (prior art) is a close up of the severed medial rectus muscle having a suture loop therein.
Figure 7:
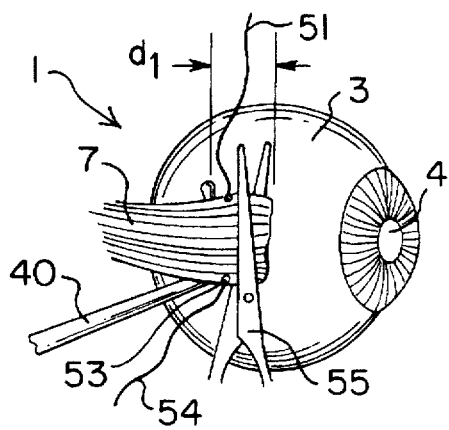
FIG. 7 (prior art) is a right side perspective view as in FIG. 4 showing the traditional suture method of strabismus surgery.
Figure 8:
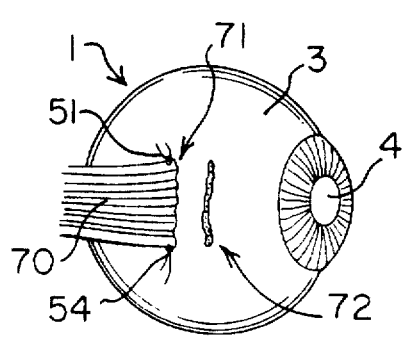
FIG. 8 (prior art) is the same as FIG. 7 showing the medial rectus muscle stitched to its new insertion.
Figure 9:
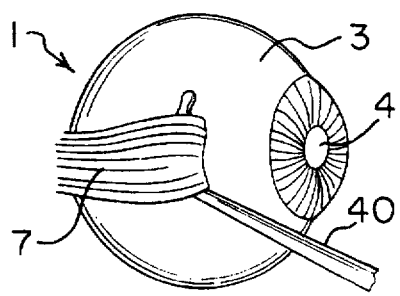
FIG. 9 (prior art) is the same view as FIG. 4.
Figure 10:
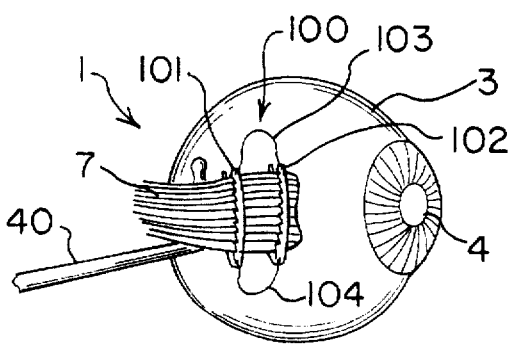
FIG. 10 (prior art) is a right side perspective view of the globe of FIG. 9 having a pair of Lingua clips attached to the medial rectus muscle.
Figure 11:
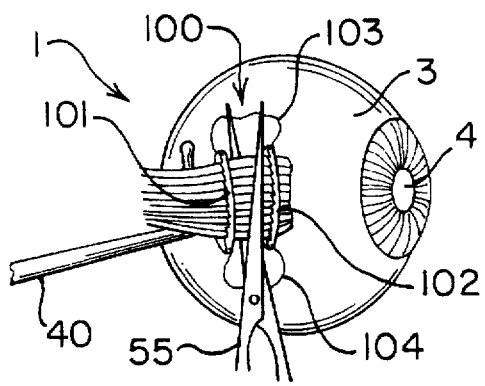
FIG. 11 (prior art) is the same as FIG. 10 showing the cutting of the medial rectus muscle.
Figure 12:
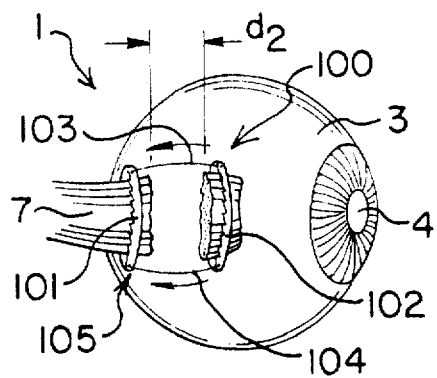
FIG. 12 (prior art) is the same as FIG. 11 showing the severed medial rectus muscle over its new insertion.
Figure 13:
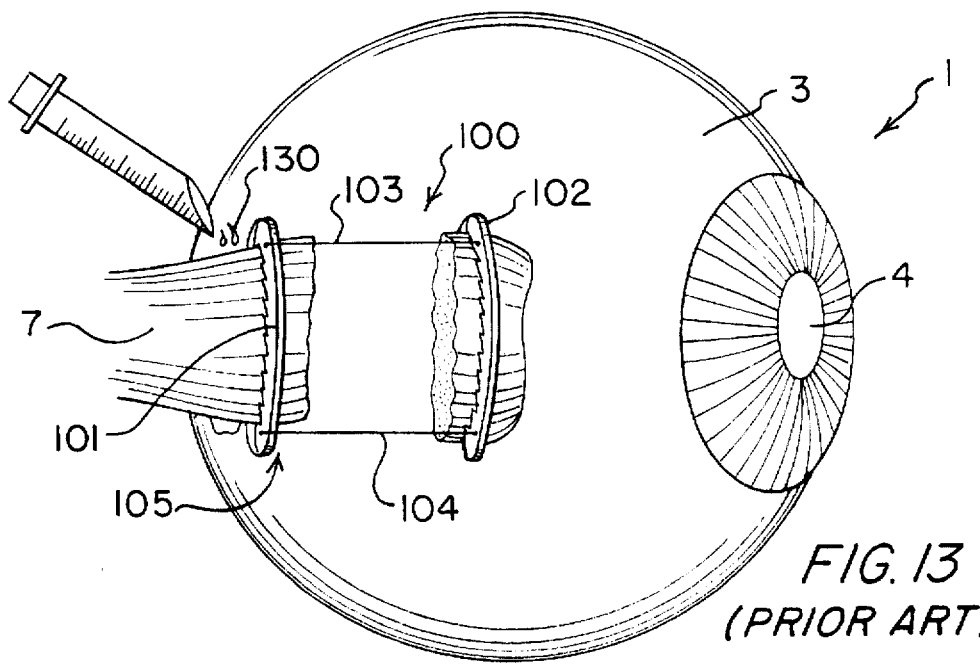
FIG. 13 (prior art) is the same as FIG. 12 showing the application of tissue adhesive to the new insertion.
Figure 14:
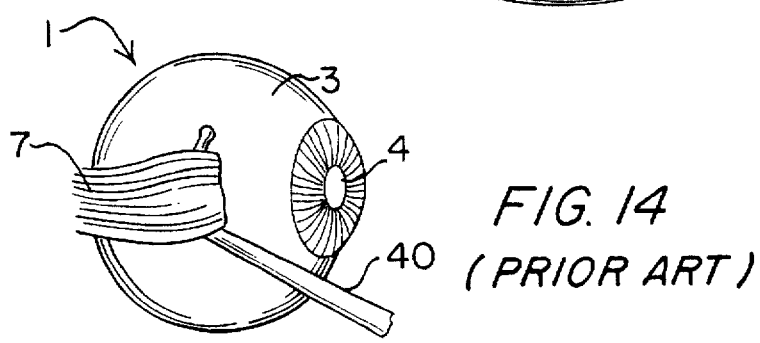
FIG. 14 (prior art) is the same as FIGS. 4 and 9.
Figure 15:
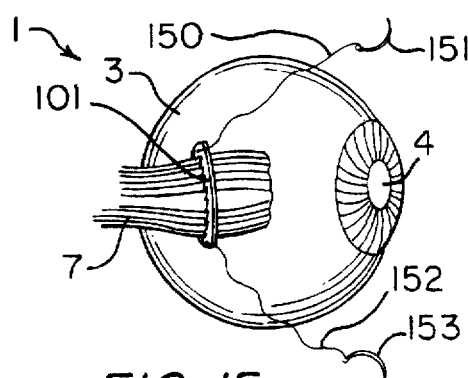
FIG. 15 (prior art) is the same as FIG. 14 showing a single Lingua clip fastened to the medial rectus muscle.
Figure 16:
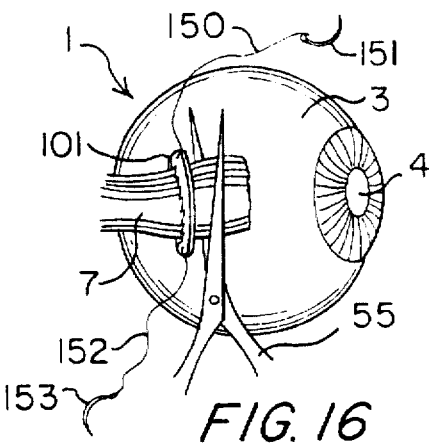
FIG. 16 (prior art) is the same as FIG. 15 showing the cutting of the medial rectus muscle.
Figure 17:
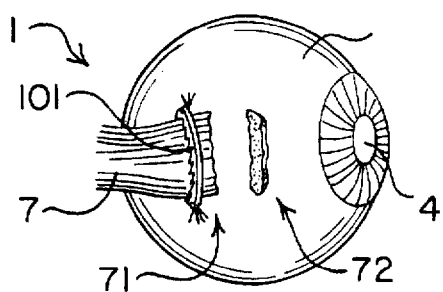
FIG. 17 (prior art) is the same as FIG. 16 showing the severed medial rectus muscle stitched to the new insertion.
Figure 22:
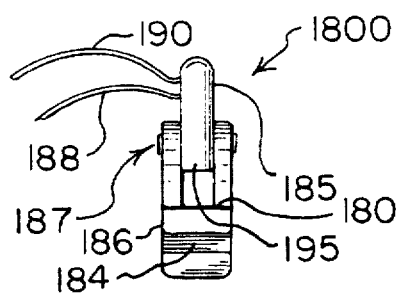
FIG. 22 is a front plan view of the Lingua clip.

Referring next to FIG. 22 shown is the lower jaw 186 of the Lingua clip 1800. Shown is the upper jaw 185 of the Lingua clip 1800.

Referring next to FIGS. 19, 20 an eye hook 1900 has a handle 1901 supporting a V-shaped hook 1910 having an upper let 1902 and a lower let 1903. These upper and lower legs provide a muscle engaging surface 1950 and 1904 respectively.

Groove 2001 in upper leg 1902 houses the upper jaw 185 of Lingua clip 1800. The groove 2001 has a width slightly larger than the upper jaw to allow the upper jaw 185 to snugly fit into groove 2001.

Groove 2000 in lower leg 1903 houses the lower jaw 186 of Lingua clip 1800. The groove 2000 has a width slightly larger than the lower jaw to allow the lower jaw 186 to snugly fit into groove 2000.

The Strabismus surgery comprises the steps of:

inserting a muscle clip into a groove in the muscle-engaging surface of an eye hook;

inserting the eye hook under a muscle;

removing the muscle clip from the eye hook;

locking the muscle clip to the muscle;

severing the muscle; and suturing the muscle clip to a desired insertion.

Referring next to FIG. 21 a resection procedure is shown which is used to strengthen the muscle 7 by making it shorter a distance of d10. Muscle section 700 is removed after the muscle clip 1800 is locked to the muscle. Then the muscle clip 1800 is sutured to the original insertion 72.

Although the present invention has been described with reference to preferred embodiments, numerous modifications and variations can be made and still the result will come within the scope of the invention. No limitation with respect to the specific embodiments disclosed herein is intended or should be inferred.

I claim:

1. An extraocular muscle clip comprising:

a hinge means at one end;

a pair of oppositely facing jaws, said jaws being interconnected at said hinge means and having opposed faces surfaced with a muscle grabbing means, at least one of said jaws having an exterior surface adjacent the eye in use;

a locking means at a second end whereby said jaws may be closed thereby securely clamping onto said muscle;

a pair of suture material members affixed to said clip;

a suture needle affixed to each of said suture material members; and said pair of oppositely facing jaws having a lower jaw member and an upper jaw member, said lower jaw member having a smooth upper surface, thereby providing a minimal resistance when passed under a muscle, said lower jaw member having recesses for receiving said upper jaw member.

2. The clip of claim 1, wherein said muscle grabbing means further comprises teeth disposed on oppositely facing surfaces of said jaws.

3. The muscle clip of claim 1, wherein said exterior surface further comprises an arcuate shape to substantially conform to the curvature of the eye.

4. A multi-purpose eye hook comprising:

a handle having a V-shaped muscle engaging surface; and said V-shaped muscle engaging surface having a groove means functioning to secure a muscle clip for passing the muscle clip under a muscle.

5. The eye hook of claim 4, in combination with a muscle clip, wherein said muscle clip comprises:

a hinge means at one end;

a pair of oppositely facing jaws, said jaws being interconnected at said hinge means and having opposed faces surfaced with a muscle grabbing means, at least one of said jaws having an exterior surface adjacent the eye in use;

a locking means at a second end whereby said jaws may be closed thereby securely clamping onto said muscle;

a pair of suture material members affixed to said clip;

a suture needle affixed to each of said suture material members; and said pair of oppositely facing jaws having a lower jaw member having a smooth upper surface.

6. The combination of claim 5, wherein said muscle clip is formed of substances approved for eye surgery selected from the group consisting of inert plastic and silicone.

7. The combination of claim 5, wherein said muscle clip is formed of nontoxic, deformable, absorbable, sterile material.

8. The combination of claim 5, wherein said muscle grabbing means further comprises teeth disposed on oppositely facing surfaces of said jaws.

9. A method to perform Strabismus surgery comprising the steps of:

inserting a muscle clip into a groove in the muscle-engaging surface of an eye hook;

inserting the eye hook under a muscle;

removing the muscle clip from the eye hook;

locking the muscle clip to the muscle;

severing the muscle; and suturing the muscle clip to a desired insertion.

* * * * *